United States Patent [19]

Federicksen et al.

[11] Patent Number: 5,106,617
[45] Date of Patent: Apr. 21, 1992

[54] METHOD OF TREATING IMMATURE BIRDS WITH IL-2

[75] Inventors: Tommy L. Federicksen, Cary, N.C.; J. Paul Thaxton, Brandon, Miss.

[73] Assignee: Embrex, Inc., Research Triangle Park, N.C.

[21] Appl. No.: 469,951

[22] Filed: Jan. 25, 1990

Related U.S. Application Data

[63] Continuation-in-part of Ser. No. 372,681, Jun. 27, 1989, Pat. No. 5,028,421, which is a continuation-in-part of Ser. No. 357,529, May 25, 1989, abandoned.

[51] Int. Cl.$^5$ .............................................. A61K 37/02
[52] U.S. Cl. ................................... 424/85.2; 530/351
[58] Field of Search ....................... 424/85.2; 530/351

[56] References Cited

FOREIGN PATENT DOCUMENTS 0293180 3/1988 United Kingdom .

OTHER PUBLICATIONS

Michael T. Lotze, MD, Yvedt L. Matory, MD, Anthony A. Rayner, MD, Stephen E. Ettinghausen, MD, John T. Vetto, MD, Claudia A. Seipp, RN, and Steven A. Rosenberg, MD, PhD, "Clinical Effects and Toxicity of Interleukin-2 in Patients with Cancer", *Cancer*, 58:2764–2772, (1986).
John A. Thompson, Douglas J. Lee, Catherine G. Lindgren, Lynn A. Benz, Carolyn Collins, William P. Shuman, Daniel Levitt and Alexander Fefer, "Influence of Schedule of Interleukin 2 Administration on Therapy with Interleukin 2 and Lymphokine Activated Killer Cells", *Cancer Research*, 49:235–240, (1989).
Dusan Kotasek, George M. Vercellotti, Augusto C. Ochoa, Fritz H. Bach, James G. White and Harry S. Jacob, "Mechanism of Cultured Endothelial Injury Induced by Lymphokine-Activated Killer Cells", *Cancer Research*, 48:5528–5532, (1988).
Tomohide Tamura, Yasutsuna Sasaki, Tetsu Shinkai, Kenji Eguchi, Masanori Sakurai, Yasuhiro Fujiwara, Kazuhiko Nakagawa, Koichi Minato, Masami Bungo, and Nagahiro Saijo, "Phase I Study of Combination Therapy with Interleukin 2 and β-Interferon in Patients with Advanced Malignancy", *Cancer Research*, 49:730–735, (1989).
Moshe Z. Papa, John T. Vetto, Stephen E. Ettinghausen, James J. Mule and Steven A. Rosenberg, "Effect of Corticosteriod on the Antitumor Activity of Lymphokine-Activated Killer Cells and Interleukin 2 in Mice", *Cancer Research*, 46:5618–5623, (1986).
Steven K. Jacobs, Debra J. Wilson, Paul L. Kornblith and Elizabeth A. Grimm, "Interleukin-2 or Autologous Lymphokine-Activated Killer Cell Treatment of Malignant Glioma: Phase I Trail", *Cancer Research*, 46:2101–2104, (1986).
Kirk C. Klasing and Barbara J. Johnstone, "Monokines in Growth and Development", *Poultry Science*, 70:1781–1789, (1991).
James W. Mier, Eugene P. Brandon, Peter Libby, Maria W. Janicka and Frederick R. Aronson, "Activated Endothelial Cells Resist Lymphokine-Activated Killer Cell-Medicated Injury", *Journal of Immunology*, 143:2407–2414, (1989).
Frederick R. Aronson, Peter Libby, Eugene P. Brandon, Maria W. Janicka, and James W. Mier, "IL-2 Rapidly Induces Natural Killer Cell Adhesion to Human Endothelial Cells", *The Journal of Immunology*, 141:158–163, (1988).
Steven A. Rosenberg, Michael T. Lotze, Linda M. Muul, Susan Leitman, Alfred E. Chang, Stephan E. Ettinghausen, Yvedt L. Matory, John M. Skibber, Eitan Shiloni, John T. Vetto, Claudia A. Seipp, Colleen Simpson, Cheryl M. Reichert, "Observations on the Systemic Administration of Autologous Lymphokine-Activated Killer Cells and Recombinant Interleukin-2 to Patients with Metastatic Cancer", *New England Journal of Medicine*, 313:1485–1492, (1985).
Lotze et al., The J. of Immunology, vol. 135, No. 4, Oct. 1985, pp. 2865–2875.
Fox, G. et al., 15th Southeastern Immunology Conference, Stone Mountain Inn, Georgia, Oct. 20–22, 1982, (Abstract).
Fredericksen, T. and Sharma, J., *Avian Immunology*, 145, (W. Weber and D. Ewert eds.), (1987).
Garland, J. and Hardie, A., *Lymphokine Res.*, 3, No. 4, 244, (1984).
Garman, R. et al., *Lymphokone Res.*, 3, No. 4, 244 (1984).
Gillis, S., *Journal of Clinical Immunology*, 3, No. 1, 1, (1983).
Krömer, G. et al., *Journal of Immunological Methods*, 73, 273, (1984).
Riendeau, D. et al., *The Journal of Biological Chemistry*, 258, 12114, (1983).
Schat, K. et al., *Avian Pathology*, 15, 539, (1986).
Schauenstein, K. et al., *Lymphoid Cell Functions in Aging*, 3, 141, (1984).
Schauenstein, K. and Hayari, Y., *Developmental and Comparative Immunology*, 7, No. 4, 767, (1983).
Schauenstein, K. et al., *Developmental and Comparative Immunology*, 6, 533, (1982).
Schnetzler, M. et al., *Eur. J. Immunol.*, 13, 560, (1983).
Vainio, O. et al., *Scand. J. Immunol.*, 23, 135, (1986).

*Primary Examiner*—Howard E. Schain
*Assistant Examiner*—Choon Park Koh
*Attorney, Agent, or Firm*—Bell, Seltzer, Park & Gibson

[57] ABSTRACT

A method of causing an animal to gain weight by administering that animal a T-cell growth factor comprising Interleukin-2 (IL-2) in an amount effective to cause that animal to increase in weight is disclosed. A method of treating birds by administering birds in ovo avian IL-2 is also disclosed. The method is preferably carried out on chicken with 30K chicken IL-2 on about the eighteenth day of incubation. The method may be employed to increase the weight of treated birds after hatch. A vaccine may optionally be administered concurrently with the avian IL-2.

3 Claims, No Drawings

METHOD OF TREATING IMMATURE BIRDS WITH IL-2

RELATED APPLICATIONS

This application is a continuation-in-part of copending application Ser. No 07/372,681, filed June 27, 1989, now U.S. Pat. No. 5,028,421 which is a continuation-in-part of copending application Ser. No. 357,529, filed May 25, 1989, now abandoned.

FIELD OF THE INVENTION

This invention relates to the treatment of animals, particularly birds, by the administration of avian Interleukin-2, with or without the concurrent administration of a vaccine, to achieve biological effects such as an increase in weight.

BACKGROUND OF THE INVENTION

Avian Interleukin-2 (IL-2) was first identified by Schauenstein et al., *Dev. and Comp. Immunol.* 6, 533 (1982), who showed the presence of a T-cell growth factor in the supernatant of mitogen-stimulated chicken spleen cells. See also Schat et al., *Avian Pathology* 15, 539 (1986); Schauenstein et al., in *Lymphoid Cell Functions in Aging*, 141–147 (A. deWeck ed. 1984); Fox et al., Abstract of Paper Presented at 15th Southeastern Immunology Conference, Stone Mountain Inn, GA, Oct. 20–22, 1982.

Avian IL-2 has subsequently been isolated, to varying degrees of purity, by Schnetzler et al., *Eur. J. Immunol*, 13, 560 (1983), Vainio et al., *Scand. J. Immunol*, 23, 135 (1986), and Fredericksen and Sharma, in *Avian Immunology*, 145–156 (W. Weber and D. Ewert eds. 1987); See also European Patent Application No. 88304729.2. This work, primarily with chicken IL-2, has demonstrated that the lymphokine exists in two configurations: a 13,000 to 14,000 Kilodalton species (hereinafter referred to as "14K chicken IL-2") and a 26,000 to 30,000 Kilodalton species (hereinafter referred to as "30K chicken IL-2").

While considerable work has been done in characterizing the T-cell growth activity of chicken IL-2 in cell culture studies, and work in non-avian species suggests that avian IL-2 may have interesting biological properties when administered to animals, See, e.g., Gillis, *J. Clin. Immunol*, 3, 1–13 (1983), there has been little mention of a practical use for avian IL-2 in vivo. It would, however, be extremely useful to know if any useful biological effect could be achieved by administering IL-2 to birds.

The present invention arose from our investigations into the biological activity of avian IL-2 in vivo. A particularly important finding disclosed herein is that, when avian IL-2 is administered to birds in ovo, the growth of the treated bird after hatch, as measured by weight gain, is enhanced.

SUMMARY OF THE INVENTION

A method of treating birds is disclosed herein. The method comprises administering to a bird in ovo a biologically active amount of avian Interleukin-2 (IL-2).

Another aspect of the present invention is a method of enhancing the growth of a bird. This method comprises administering avian IL-2 to a bird in ovo in an amount effective to enhance the growth of the bird after hatch.

Another aspect of the present invention is a method of treating birds, which method comprises concurrently administering avian IL-2 and a vaccine to a bird in ovo. The vaccine is administered in an amount effective to produce active immunity in the bird; the IL-2 is administered in an amount effective to (a) enhance the growth of the bird after hatch, (b) enhance the degree of immunity produced by the vaccine, or (c) both enhance the growth of the bird after hatch and enhance the degree of immunity produced by the vaccine.

Another aspect of the present invention is an egg injection apparatus for use in the automated injection of bird eggs with avian IL-2. The apparatus comprises an injector and an egg holder operatively associated with the injector. The egg holder and the egg injector are each connected to a common supporting frame. The injector contains an injection liquid, with the injection liquid containing avian IL-2. The injector is positioned for injecting an egg carried by the egg holder with the injection liquid. The injector is configured to deliver a biologically active amount of avian IL-2 to the egg. Preferably, the apparatus also comprises a punch operatively associated with the injector for providing a hole in the egg's shell prior to injection, through which hole the injector is inserted. A vaccine may optionally be included in the injection liquid.

Another aspect of the present invention is a fertile bird egg having deposited therein a biologically active amount of exogenous avian IL-2. The egg may also optionally contain a vaccine.

The present invention provides the first demonstration in any animal that an immune factor will influence growth. Thus, the present invention provides a method of inducing an animal to gain weight, comprising administering to said animal Interleukin-2 (IL-2) in an amount effective to cause the animal to increase in weight. Preferably, animals treated to induce a gain in weight are immature animals (i.e., not adult).

DETAILED DESCRIPTION OF THE INVENTION

The term "animals," as used herein, is intended to include, among other things, both mammals and birds. Exemplary mammals include mice, rats, guinea pigs, rabbits, ferrets, dogs, cats, cows, horses and primates including man. The term "bird" is intended to include males or females of any avian species, but is primarily intended to encompass poultry which are commercially raised for eggs or meat. Accordingly, the term "bird" is particularly intended to encompass hens, cocks and drakes of chickens, turkeys, ducks, geese, quail and pheasant. Birds are preferred.

The term "interleukin-2" (or "IL-2"), as used herein, refers to any interleukin-2, whether of bovine, ovine, murine, human, or avian origin. Numerous kinds of IL-2 and methods for their preparation are available. See U.S. Pat. No. 4,404,280 to Gillis; U.S. Pat. No. 4,411,992 to Gillis; U.S. Pat. No. 4,401,756 to Gillis; U.S. Pat. No. 4,448,879 to Fabricius and Stahl; U.S. Pat. No. 4,464,355 to Fabricius and Stahl; U.S. Pat. No. 4,473,642 to Gillis (the disclosures of all patent references cited herein are to be incorporated herein by reference). Preferably, when practicing the present invention, the IL-2 administered is related in origin to the species to which it is administered. Thus, it is preferred to administer mammalian IL-2 to mammals and preferred to administer avian IL-2 to birds. Among the mammals, it is known that IL-2 from some species will be active in some other species but not in other species. Those skilled in the art will be able to select an appropriate IL-2 composition for the animal being treated based on the known cross-reactivities of IL-2 and simple screening tests known to those skilled in the art.

The term "in ovo," as used herein, refers to birds contained within an egg prior to hatch. Thus, the present invention may be conceived of as both a method of treating eggs and a method of treating birds. The present invention may be practiced with any type of bird egg, including chicken, turkey, duck, goose, quail, and pheasant eggs. Chicken and turkey eggs are preferred, with chicken eggs most preferred. Eggs treated by the method of the present invention are fertile eggs which are preferably in the fourth quarter of incubation. Chicken eggs are treated on about the fifteenth to nineteenth day of incubation, and are most preferably treated on about the eighteenth day of incubation (the eighteenth day of embryonic development). Turkey eggs are preferably treated on about the twenty-first to twenty-sixth day of incubation, and are most preferably treated on about the twenty-fifth day of incubation.

The term "avian IL-2," as used herein, means IL-2 corresponding to IL-2 produced by any avian species. The term "avian" is intended to encompass all avian species, including, but not limited to, chickens, turkeys, ducks, geese, quail, and pheasant. Various species of avian IL-2 are known. See, e.g., Schnetzler et al., supra; Vainio et al., supra; Fredericksen and Sharma, supra. In brief, avian IL-2 may be obtained by collecting lymphocytes from an avian donor (most conveniently from the spleen of an avian donor), growing the lymphocytes in a medium (preferably a serum-free medium) containing a T-cell mitogenic agent such as Concanavalin A, and, optionally, recovering the IL-2 from the medium. While the degree of purity of the avian IL-2 is not critical to practicing the present invention, it is preferably at least substantially serum free and mitogen free. A crude IL-2 preparation may be purified by any of a variety of known separation procedures, with various fractions from these procedures being screened for IL-2 activity by IL-2 assay procedures known in the art. The IL-2 may be provided in any suitable pharmaceutically acceptable carrier, but is preferably provided in an aqueous carrier such as a phosphate-buffered saline solution.

The cross-reactivity of IL-2 of various avian species can be routinely determined with known bioassay procedures employing IL-2 responder cells, see. e.g., Schnetzler et al., supra at 561, or can simply be screened by administering to a sample group of birds in ovo an IL-2 for which activity in that species is to be determined. In general, it is to be expected that, the closer the species of origin of the IL-2 administered to the avian species being treated in any one case, the greater the biological activity of the IL-2 in that subject. Hence, it is preferred, but not essential, that the IL-2 being administered in the method disclosed herein correspond in species of origin to the avian subject being treated. The quantity of IL-2 administered per egg will vary according to the species being treated, the species of IL-2 origin, the subject's age, the site of injection in the egg, and the purity of the IL-2.

Chicken IL-2, as discussed above, exists as a 14K species and a 30K species. See Fredericksen and Sharma, supra; Schnetzler, supra at 565. The 30K species is believed to be the native form, has in our hands greater activity in vitro, and is currently preferred for practicing the present invention. One milligram of avian IL-2 which is determined to be 97% pure by HPLC provides from about 1,000 to about 10,000 Activity Units of avian IL-2, as determined by the procedures set forth in the Examples which follow. For practicing the present invention, avian IL-2 is administered in an amount of from about 0.001 to about 10 Activity Units per egg, and more preferably administered in an amount of from about 0.005 to about 1 Activity Units per egg. For example, positive results with the method of the present invention are expected in chickens administered 30K chicken IL-2 on about the 18th day of incubation with dosages ranging between about 100 nanograms per egg and about 1.0 nanograms per egg for IL-2 that is at least about 50% pure.

Insofar as this applicant is aware, analogs of avian IL-2 have not yet been synthesized. However, based on the cross-reactivity of various IL-2s in non-avian species, it is expected that synthetic analogs of avian IL-2, when available, can be screened for activity in the present invention in a routine manner, and should function in the present invention in substantially the same way as the naturally occuring IL-2s.

The present invention may be practiced in conjunction with the methods disclosed in U.S. Pat. No. 4,458,630 to Sharma and Burmester and European Patent Application No. 0 291 173 to Smith et al., the disclosures of which are incorporated herein by reference. Thus, a vaccine may be administered concurrently with the IL-2. The term "vaccine," as used herein, is intended to encompass both live vaccines as discussed in the Sharma and Burmester patent and nonreplicating vaccines as discussed in the Smith et al. application. Exemplary live vaccines include, but are not limited to, turkey herpes virus vaccine (HVT), and the Bursal Disease Vaccine, Lukert strain, live virus, which is obtained from either Vineland Laboratories in Vineland, New Jersey or Salsbury Laboratories in Charles City, Iowa. Exemplary nonreplicating vaccines (i.e., nonreplicating immunogens) include, but are not limited to, killed viruses, peptides, proteins (including protein sub-unit immunogens such as those produced by genetic engineering techniques), peptides bound to carriers, and anti-idiotipic antibodies, all of which are incapable of reproducing themselves in a subject. Specific examples of nonreplicating vaccines are given in U.S. Pat. Nos. 4,639,372 to Murray et al. and 4,724,145 to Murray et al., and in European Patent Application No. 0 241 139, the disclosures of which are incorporated herein by reference. For most common avian diseases, the known vaccines which are either live vaccines or nonreplicating vaccines intended for post-hatch administration would be used in accordance with the methods disclosed herein, adjusting the dosage as necessary.

Administration of IL-2 to animals may be carried out by any suitable means, such as by intravenous injection, intraperitoneal injection, and subcutaneous injection.

Eggs may be administered IL-2 by any means which transports the compound through the shell. The preferred method of administration is, however, by injection. The site of injection is preferably within either the region defined by the amnion, including the amniotic fluid and the embryo itself, in the yolk sac, or in the air cell. By the beginning of the fourth quarter of incubation, the amnion is sufficiently enlarged that penetration thereof is assured nearly all of the time when the injection is made from the center of the large end of the egg along the longitudinal axis. The vaccine may be administered by the same means and to the same location as the IL-2.

The mechanism of injection is not critical, but it is preferred that the method not unduly damage the tissues and organs of the embryo or the extraembryonic membranes surrounding it so that the treatment will not decrease hatch rate. A hypodermic syringe fitted with a needle of about 18 to 22 gauge is suitable for the purpose. To inject into the air cell, the needle need only be inserted into the egg by about two millimeters. A one inch needle, when fully inserted from the center of the large end of the egg, will penetrate the shell, the outer and inner shell membranes enclosing the air cell, and the amnion. Depending on the precise stage of development and position of the embryo, a needle of this length will terminate either in the fluid above the chick or in the chick itself. A pilot hole may be punched or drilled through the shell prior to insertion of the needle to prevent damaging or dulling of the needle. If desired, the egg can be sealed with a substantially bacteria-impermeable sealing material such as wax or the like to prevent subsequent entry of undesirable bacteria.

It is envisioned that a high speed automated injection system for avian embryos will be particularly suitable for practicing the present invention. Numerous such devices are available, exemplary being those disclosed in U.S. Pat. No. 4,681,063 to Hebrank and U.S. Pat. Nos. 4,040,388, 4,469,047, and 4,593,646 to Miller (the disclosures of all U.S. patent references cited herein are to be incorporated herein by reference). All such devices, as adapted for practicing the present invention, comprise an injector containing avian IL-2 as described herein, with the injector positioned to inject an egg carried by the apparatus with the avian IL-2. Other features of the apparatus are discussed above. In addition, if desired, a sealing apparatus operatively associated with the injection apparatus may be provided for sealing the hole in the egg after injection thereof.

Preferred apparatus for practicing the present invention is disclosed in U.S. Pat. No. 4,681,063 to Hebrank and European Patent Application No. 87305746.7 to Embrex, Inc., filed 29 June 1987, the disclosures of which are incorporated herein by reference. This device comprises an injection apparatus for delivering fluid substances into a plurality of eggs and suction apparatus which simultaneously engages and lifts a plurality of individual eggs from their upwardly facing portions and cooperates with the injection means for injecting the eggs while the eggs are engaged by the suction apparatus. The features of this apparatus may be combined with the features of the apparatus described above for practicing the present invention.

The phrase "concurrently administered, as used herein, means that the IL-2 and the vaccine are administered in the same period of time (e.g., during the last quarter of in ovo incubation). Preferably, the IL-2 and the vaccine are administered at substantially the same time. Most preferably, the IL-2 and the vaccine are administered simultaneously by formulating the two together in a single pharmaceutically acceptable carrier.

The following examples are provided to more fully illustrate the present invention, and are not to be taken as restrictive thereof.

EXAMPLE 1

Preparation of Spleen Cells

Spleens were obtained from Hyline, SC chickens between 4 and 10 weeks of age, and a single cell suspension prepared from decapsulated spleen. Specifically, the spleen was placed in phosphate buffered saline (PBS) (pH=7.4), passaged through a five millimeter syringe barrel, and then passaged through an eighteen gauge needle. The suspension was held at room temperature for five minutes to allow the stroma to settle and the supernatant was collected. An additional five milliliters of PBS was added to the settled stroma, mixed, held for five minutes, and the supernatant was collected and pooled with the first supernatant. These cells were then pelleted and washed twice with PBS before adding RPMI-G medium, as explained in Example 2 below. Cell viability was greater than 95% as measured by trypan blue dye exclusion.

EXAMPLE 2

Preparation of Conditioned Medium

RPMI-G medium consisted of RPMI-1640 media supplemented with L-glutamine (2 mM), and gentamicin sulfate (50 micrograms per milliliter)(Sigma, St. Louis, MO).

Single-cell suspensions from spleen were placed into 75 square centimeter flasks with 50 milliliters of RPMI-G medium at a cell concentration of 6 times $10^6$ cells per milliliter and a Concanavalin A (Sigma Chemical Co., St. Louis, MO) concentration of 4 micrograms per milliliter. Conditioned Medium (CM) was obtained from these cultures following incubation at 40 degrees Centigrade in a humidified atmosphere with 5% $CO_2$ for 64–96 hours, with peak production being obtained after 96 hours.

EXAMPLE 3

Production of IL-2

After incubation, the conditioned medium described in Example 2 above was centrifuged in 50 milliliter conical tubes to separate supernatant from cells. The supernatant was removed and used as the source of IL-2; the cells were saved for use in a bioassay for IL-2 activity. The supernatant was concentrated on 10,000 molecular weight membrane filters (Amicon) and the concentrated supernatant was then subjected to HPLC gel filtration using a G2000 SW TSK column (300 by 7.5 millimeters) with an elution buffer of PBS. The flow rate was one milliliter per minute. Fractions were concentrated with a "CENTRICON" concentrating device having a 10,000 molecular weight cutoff filter. The typical retention time for the avian IL-2 peak was 8.2 to 8.8 minutes. Calibration with molecular weight standards indicate the average species has a molecular weight of 30±6 Kilodaltons.

EXAMPLE 4

Assay of IL-2 Activity

The cells saved for assay in Example 3 above are used as IL-2 responder cells. The cells are fractionated on a 20–60% "PERCOLL" gradient (4 milliliters of 60%, then 5 milliliters of 20%) by layering the cells on the gradient, with one gradient per flask using 17 by 100 centimeter centrifuge tubes, centrifuging the tubes at 1600 RPMs for ten minutes, and removing the cells from the 60% interface. The cells are then washed twice with PBS and RPMI-G added as a diluent. The cells are counted and the final cell concentration adjusted to 2.0 times $10^6$ cells per milliliter, with the medium containing 0.1 M alpha-methyl-D-mannopyranoside (Siqma) to inaotivate residual mitogen, to provide a responder cell solution.

100 microliters of the responder cell solution is dispensed into each well of a 96-well microculture plate, with each well also containing 100 microliters of test IL-2 solution. After 22 hours of incubation, 20 microliters of 3-(4,5-dimethylthiazolyl-2)-2,5-diphenyl tetrazolium bromide (MTT) solution at a concentration 5 milligrams per milliliter is added to each well and the plate incubated for an additional three hours. 100 microliters of medium is then removed from each well (without shaking the plates), 100 microliters of acid isopropanol added to each well, the wells mixed, and the contents read on an ELISA reader such as a Dynatech MR650 automated microplate reader at wavelength 570 nanometers. A reference conditioned medium containing IL-2 from grown cells is arbitrarily assigned an activity of one unit per milliliter and is also incubated.

In this bioassay, MTT is broken down by the mitochondria of live T cells to a formazan. The greater the optical density of the well contents, as determined by the ELISA reader, the more formazan is present in the well, and the greater the number of T cells present in the well.

This bioassay is used to confirm the T-cell growth activity of IL-2 purified by HPLC gel filtration according to the procedure of Example 3 above.

EXAMPLE 5

Administration of IL-2 to Birds In Ovo

An IL-2 solution prepared according to Examples 1 through 3 above, determined to be 61% pure with the assay procedure described in Example 4 above, and determined to contain 88 micrograms of protein per milliliter by a BIO RAD protein assay, was used for in ovo administration. Three different IL-2 injection solutions containing active compound and PBS diluent were prepared so that, with an injection volume of 0.2 milliliters per egg, eggs could be administered 88 nanograms IL-2 per egg, 8.8 nanograms of IL-2 per egg, and 0.88 nanograms of IL-2 per egg.

Fertile Hubbard broiler eggs reared in Petersime brooders were injected with the IL-2 solutions on the eighteenth day of incubation. Seventeen to twenty-five eggs were injected with each solution. The eggs were placed in flats and injected one egg at a time to minimize cooling. A hole was punched at the long axis of the egg with an 18 guage needle adapted with a rubber stopper to allow a 2 millimeter maximum piercing depth so that the egg was injected in the air cell. The injection solution was kept in an ice bath to maintain it at about 4 degrees Centigrade, each egg injected with 0.2 milliliters of IL-2 injection solution, and the eggs then transferred to a hatcher and allowed to hatch. Male birds were weighed at hatch, maintained on food and water ad libitum in a controlled environment (Petersime brooders), and weighed at days 8 and 16 post hatch. Results are given in Table 1 below. These results indicate that in ovo administration of IL-2 to birds increases the body weight of the birds at days 8 and 16 post hatch.

TABLE 1

| Treatment | Sample | Concentration (ng/egg) | Days Posthatch Body Weight (grams) | | |
|---|---|---|---|---|---|
| | | | 0 | 8 | 16 |
| 1 | None | — | $42.3 \pm 7^a$ (14) | $177.4 \pm 4.5^a$ (14) | $447.6 \pm 8.2^a$ (14) |
| 2 | IL-2 | 88 | $43.9 \pm 9^a$ (11) [+3.8] | $189.2 \pm 4.5^a$ (11) [+6.8] | $503.3 \pm 14.2^b$ (11) [+12.4] |
| 3 | IL-2 | 8.8 | $43.2 \pm 1.2^a$ (11) [+2.1] | $198.2 \pm 3.2^b$ (11) [+11.9] | $517.3 \pm 9.2^b$ (11) [+15.6] |
| 4 | IL-2 | .88 | $42.2 \pm .9^a$ (11) [−0.2] | $195.6 \pm 4.8^b$ (9) [+10.5] | $506.2 \pm 12.7^b$ (9) [+13.1] |

[] Percent difference in comparison with Treatment 1 [(Treatment X - Treatment 1) ÷ Treatment 1] × 100.
$a,b$Weights in columns possessing different superscripts differ significantly at $P \leq 0.5$.

EXAMPLES 6–9

Production and Assay of Turkey IL-2

These examples show the isolation of avian IL-2 from an avian species other than chicken.

Spleen cells are prepared in accordance with the procedure described in Example 1 above, except that the spleens are obtained from Nicholas White turkey toms. Conditioned Medium is prepared from these spleen cells in accordance with the procedure described in Example 2 above, and turkey IL-2 is obtained from this Conditioned Medium in accordance with the procedure described in Example 3 above. With this procedure, most of the turkey IL-2 activity is found in fraction 3, with a peak retention time of about 8.8 minutes. This retention time corresponds to an average molecular weight species of 22 Kilodaltons ±5 Kilodaltons (herein referred to as "22K Turkey IL-2"). IL-2 activity is determined by the same procedure described in Example 4 above, except turkey T-cells saved from the procedures described in the present set of examples are used instead of chicken T cells in the bioassay.

EXAMPLE 10

Cross-species Biological Activity of Avian IL-2

Turkey Conditioned Medium is tested for biological activity using activated chicken T cells, and Chicken Conditioned Medium is tested for biological activity using activated turkey T cells, all in accordance with the procedures described above. Both Conditioned Media are found to stimulate the growth of both chicken and turkey T cells, indicating substantial cross-reactivity between chicken and turkey IL-2.

EXAMPLE 11

In ovo administration of IL-2 in Combination with Marek's Disease Vaccine

This example shows that, when IL-2 is administered In ovo in combination with a standard In ovo vaccine dose, the growth-enhancing activity of the IL-2 is retained.

This experiment consists of five treatments as follows: (1) 0.01 microgram per egg of IL-2 with a standard dose of HVT vaccine on day 18 of incubation; (2) 0.1 microgram per egg of IL-2 with a standard dose of HVT vaccine on day 18 of incubation; (3) 1. microgram per egg of IL-2 with a standard dose of HVT vaccine on day 18 of incubation; (4) 10. micrograms of IL-2 with a standard dose of HVT vaccine on day 18 of incubation; and (5) an uninjected negative control group receiving a shell puncture only on day 18 of incubation.

The procedure for this experiment is as follows. 720 eggs are obtained from a commercial poultry company, set, incubated until day 18, injected into the amnion, hatched, wing-banded, and weighed. All birds are weighed at one week and two weeks of age as well as at hatch. The negative control group and the treatment group with the best body weight gains are grown out until six weeks and weighed at that time. For grow out, 400 chicks are housed in a 20 pen, curtain-sided broiler house that faces east to west. 20 chicks are placed in each pen; four replicate pens are used for each treatment. Birds are maintained on a standard broiler chicken ration and exposed to a 23 hours of light and one hour of dark light cycle for the duration of the experiment.

The results of an experiment as described above are given in Tables 2 to 4 below. IL-2 was prepared in accordance with Example 3 above, and was determined to be 97% pure by HPLC.

TABLE 2

Growth Effect of In Ovo Administration of IL-2 in Combination with HVT Vaccine[1]

| Trt # | IL-2 (μg/egg) | Hatchability | Mean Body Weight (weeks) | | | |
|---|---|---|---|---|---|---|
| | | | 0 | 1 | 2 | 3 |
| 1 | 0.01 | 95.2 [99][2] | 40.9 | 97 (−2.0) | 231 (0)[3] | NT |
| 2 | 0.1 | 96.6 [112] | 41.1 | 102 (3.0) | 249 (7.3) | 498 (+4.2) |
| 3 | 1.0 | 94.8 [110] | 42.1 | 101 (2.0) | 242 (4.3) | NT |
| 4 | 10 | 93.0 [109] | 41.7 | 101 (2.0) | 232 (0) | NT |
| 5 | None | 97.7 [113] | 41.2 | 99 | 232 | 478 |

[1]Except for Group 5, all other administrations were with IL-2 mixed with a standard dose (7,000 PFU/egg) of Marek's disease (HVT) vaccine.
[] = Number of chicks.
[3]() = Percent difference from Treatment 5.

TABLE 3

Growth Effect of In Ovo Administration of IL-2 in Combination with HVT Vaccine: Males Versus Females

| | | Mean Body Weight (Post Hatch) | | | | | |
|---|---|---|---|---|---|---|---|
| | | Week 4 | | Week 5 | | Week 6 | |
| Trt # | IL-2 | Male | Female | Male | Female | Male | Female |
| 2 | 0.1 | 1036 (+17.8) | 702 (−9.0) | 1385 (+1.7) | 1231 (+2.5) | 1907[b] (+3.7) | 1598[a] (0) |
| 5 | None | 880 | 772 | 1371 | 1201 | 1839[a] | 1602[a] |

[a,b]Statistically different at P ≤ .05.

TABLE 4

Effect of In Ovo Administration of IL-2 in Combination with HVT Vaccine on Feed Conversion Ratios

| Trt | IL-2 μg/egg | Feed Conversions (gms/bird) Week NO. | | | | | |
|---|---|---|---|---|---|---|---|
| | | 1 | 2 | 3 | 4 | 5 | 6 |
| 1 | .01 | 1.128 | 1.573 | | | | |
| 2 | 0.1 | 1.093 | 1.510 | 1.417 | 1.302 | 1.481 | 1.950 |
| 3 | 1.0 | 1.182 | 1.577 | | | | |
| 4 | 10.0 | 1.094 | 1.559 | | | | |
| 5 | None | 1.202 | 1.641 | 1.398 | 1.296 | 1.462 | 1.958 |

Mean body weights for each group are given for the first three weeks after hatch in Table 2. Treatment group 2 was selected for grow-out. Data for groups 2 and 5 at the fourth, fifth, and sixth week after hatch is given in Table 3. Note that, at six weeks after hatch, males in treatment group 2 had significantly greater (p≤0.05) body weights than males in control group 5. Feed conversion data for groups 1 through 5 is given in Table 4. Note the improved feed conversion ratio for the IL-2 treated group.

EXAMPLES 12-14

Enhanced Cell-Mediated Immunity to Bovine Serum Albumin by Co-administration In ovo with IL-2

This example demonstrates the effect of In ovo IL-2 on T cell immunity to an antigen administered in ovo after hatch.

Bovine serum albumin (BSA) is administered as an antigen on day 18 of incubation by injection into the amnion. Eggs are manually injected with antigen prepared in a 200 microliter volume. The injection depth is 26 millimeters from the top, into the large end of the eggs, using a one inch 21 gauge needle inserted full length. Spleens are collected from birds which hatch from the injected eggs and used to measure in vitro T-cell proliferative response to BSA with the MTT-dye assay described in Example 4 above.

Four different treatment groups were tested in vitro for spleen T-cell proliferative response: (1) a group receiving 2 micrograms of BSA in ovo; (2) a group receiving 20 micrograms of BSA in ovo; (3) a group receiving 200 micrograms of BSA in ovo; and (4) a vehicle-injected negative control group. Phosphate buffered saline was used as the vehicle. Spleens (3-4 per group) were taken from donors in each group at day 16 post hatch, thereby allowing sufficient time for memory cells to develop. Cell suspensions were made and these cells plated out in triplicate into 96-well microculture plates. For each of the groups tested, three types of in vitro treatments were employed: (1) negative control, cells given no antigen; (2) positive control, cells given Concanavalin A (0.5 to 1 microgram per well) to provide the maximum response possible under these conditions; and (3) triplicates given twofold increasing doses of BSA antigen beginning with 0.625 micrograms per well. Antigen and Concanavalin A were added in 0.1 milliliter volumes. This latter group simulated rechallenge with antigen in vivo. Proliferation was assessed two days after challenge. Pooled data from 3 to 5 tests conducted as described above is given in Table 5. The response of the negative controls is 12% of maximum proliferation. There is relatively no change in response of cells from the negative control group to BSA in culture except for cells given the highest dose of BSA. Cells from birds that received 2 and 200 micrograms of BSA in ovo showed a linear dose response from BSA concentrations of 1 to 10 micrograms. The peak is 30% of the maximum proliferation, or 2.5 times more than the negative control. The response from cells from birds administered 20 micrograms of BSA in ovo is suppressed.

TABLE 5

In Vitro T Cell Response from Chicks Administered BSA In Ovo

μg/well BSA

| | .625 | 1.25 | 2.5 | 5.0 | 10.0 | 20 | 40 | 80 |
|---|---|---|---|---|---|---|---|---|
| Percent Con A Response of Control Group | | | | | | | | |
| Mean | 7.42 | 13.38 | 17.34 | 12.98 | 11.14 | 9.36 | 15.48 | 23.16 |
| Standard Error of Mean | 3.64 | 8.39 | 5.83 | 3.76 | 2.31 | 4.32 | 5.79 | 5.65 |
| Valid N | 5 | 5 | 5 | 5 | 5 | 5 | 5 | 5 |
| Percent Con A Response of 200 μg in ovo Group | | | | | | | | |
| Mean | 8.32 | 15.35 | 23.50 | 22.05 | 26.05 | 22.98 | 21.03 | 21.88 |
| Standard Error of Mean | 4.53 | 8.65 | 6.25 | 5.26 | 4.81 | 4.08 | 4.58 | 4.19 |
| Valid N | 4 | 4 | 4 | 4 | 4 | 4 | 4 | 4 |
| Percent Con A Response of 20 μg in ovo Group | | | | | | | | |
| Mean | 11.22 | 12.54 | 3.83 | .42 | .10 | 9.70 | 18.50 | 21.30 |
| Standard Error of Mean | 6.84 | 9.20 | 3.72 | .32 | .00 | 5.91 | 11.59 | 9.94 |
| Valid N | 5 | 5 | 5 | 5 | 5 | 5 | 5 | 5 |
| Percent Con A Response of 2 μg in ovo Group | | | | | | | | |
| Mean | 12.00 | 18.44 | 19.30 | 25.04 | 29.30 | 29.74 | 21.26 | 24.24 |
| Standard Error of Mean | 7.54 | 7.04 | 2.00 | 1.45 | 3.21 | 5.34 | 6.39 | 10.51 |
| Valid N | 5 | 5 | 5 | 5 | 5 | 5 | 5 | 5 |

$$\text{Percent of Con A Response} = \frac{\text{OD of Response by antigen or none}}{\text{OD of optimal Con A Response}} \times 100$$

The experiment described above was repeated, except that Il-2 was co-administered in ovo with the BSA antigen. The IL-2 was 61% pure as determined by HPLC; 0.1 nanogram per egg of IL-2 was administered. Data from this experiment is given in Table 6 below. Note that the proliferative response of cells taken from birds administered 20 micrograms of BSA in ovo is enhanced two to five fold by the coadministration of IL-2.

TABLE 6

| | | Medium and High Antigen Concentrations | | | |
|---|---|---|---|---|---|
| In Vitro TC μg/well | In Ovo None | IL-2 Only IL-2 (.1ng) | Antigen Only BSA (μg egg) | | Combination IL-2 + BSA | |
| | | | 20 | 200 | 20 | 200 |
| 1.25 | 9[1] | NT | 13 | 8 | 25 | 8 |
| 2.5 | 8 | NT | 10 | 24 | 47 | 26 |
| 5 | 13 | NT | 21 | 36 | 61 | 23 |
| 10 | 23 | NT | 10 | 43 | 55 | 44 |

[1]Percent Con A Response.

The foregoing experiment was again repeated, with a dose of IL-2 as described immediately above, except that a dose of BSA of 4 nanograms per egg was used. These data are given in Table 7 below. Note that (a) the BSA only group did not show a proliferative response in vitro, (b) the IL-2 only group did not show an improved response over the control group in vitro, and (c) the coadministration group yielded a significant proliferative response in vitro.

TABLE 7

| | Percent of Maximum Con A Response | | | |
|---|---|---|---|---|
| In Vitro Conc. BSA | None | IL-2 (.1 ng) | BSA (4 μg) | BSA + IL-2 |
| 1.25 | 1 | 8.5 | 0 | 41 |
| 2.5 | 3 | 15.7 | 0 | 20 |
| 5.0 | 16.1 | 6.6 | 0 | 50 |
| 10.0 | 9.7 | 8.3 | 0 | 40 |

The foregoing examples are illustrative of the present invention, and are not to be taken as limiting thereof. The invention is defined by the following claims, with equivalents of the claims to be included therein.

That which is claimed is:

1. A method of inducing an immature bird to gain weight, comprising administering to said immature bird Interleukin-2 (IL-2) in an amount effective to cause said immature bird to increase in weight.

2. A method according to claim 1, wherein said immature bird is selected from the group consisting of chickens, turkeys, ducks, geese, quail and pheasant.

3. A method according to claim 1, wherein said administering step is carried out by means selected from the group consisting of in ovo injection, intravenous injection, intraperitoneal injection, and subcutaneous injection.

* * * * *